United States Patent [19]

Bunin

[11] Patent Number: 5,042,472
[45] Date of Patent: Aug. 27, 1991

[54] POWDER INHALER DEVICE

[75] Inventor: Leonid Bunin, Woodbridge, N.J.

[73] Assignee: Merck & Co., Inc., Rahway, N.J.

[21] Appl. No.: 597,642

[22] Filed: Oct. 15, 1990

[51] Int. Cl.⁵ .............................................. A61M 15/00
[52] U.S. Cl. ........................... 128/203.15; 128/203.12; 206/539
[58] Field of Search ...................... 128/203.15, 203.12, 128/203.23, 203.24, 203.21; 206/538, 539; 220/507, 524, 23.86

[56] References Cited

U.S. PATENT DOCUMENTS

| | | | |
|---|---|---|---|
| 2,603,215 | 7/1952 | Arnow | 128/203.15 |
| 3,738,480 | 6/1973 | Chesley | 206/539 |
| 4,216,768 | 8/1980 | Jack | 128/203.15 |
| 4,627,432 | 12/1986 | Newell et al. | 128/203.15 |

Primary Examiner—Edgar S. Burr
Assistant Examiner—Stephen R. Funk
Attorney, Agent, or Firm—Raymond M. Speer; Hesna J. Pfeiffer

[57] ABSTRACT

A powder inhaler device not requiring a propellant is disclosed which comprises a unit dose package and delivery system which is breath actuated and permits a patient to inhale through the mouth a medication in powder form for administration to the bronchia and lungs. The powder dose is contained in a compartment of the device which is sealed off from the environment by a peel-off piece of lidding material. The compartment has two apertures: one over which the mouth of the patient is placed to receive the powder medication by inhalation; and the other which permits ingress of air to aerosolize the powder medication.

4 Claims, 2 Drawing Sheets

POWDER INHALER DEVICE

BACKGROUND OF THE INVENTION

1. Field of the Invention

The present invention is in the field of devices for dispensing medicaments in powder form without the use of propellants, which are breath actuated, with the medicament dose being inhaled by mouth.

The site of administration of the powder medicament, delivered by devices of the type to which that of the present invention belongs, is the bronchial tubes and their ramifications in the lungs of the patient being treated. Thus, the bronchi and bronchioles are the primary sites of administration. Typically, such a patient may be suffering from asthma or acute or chronic bronchitis, and it is essential that the powder dose of medicament reach and be applied uniformly to as much of the surface of the bronchi and other parts of the lung as possible.

In order to achieve this objective, the powder medicament is usually in the form of extremely fine particles, preferably in the size range of from 1 to 10 microns. In order to achieve the necessary particle size distribution for the powder medicament to be used in a powder inhaler device, techniques such as controlled crystallization will be employed. One may also use anti-agglomerating agents to ensure that there is no clumping together of the extremely fine particles, which have a natural tendency to flocculate together due to the static charge which such fine particles normally acquire.

The powder medicament for use in the powder inhaler device of the present invention may also be hygroscopic in nature, causing particle aggregation while the dose is still resident in the powder inhaler device, and also causing particle growth during inhalation. Problems of hygroscopicity may be overcome by a portective coating on the medicament particles, or by use of a dessicating excipient.

Thus, the powder medicament for use in the powder inhaler device of the present invention must be fine, i.e., 1-10µ, and substantially free from any tendency to agglomerate.

The powder inhaler devices of the type to which that of the present invention belongs do not require the use of propellants, and thus represent an advance in the art over those devices which dispense metered doses of a powder medicament with the assistance of a propellant gas. Predominantly, the propellant of choice is FREON®, one of various nonflammable fluo.ocarbons. However, use of this particular propellant has been the object of recently passed environmental laws which severely restrict its use or even ban it outright. Furthermore, fluorocarbons may actually aggravate the condition of patients suffering from asthma and acute or chronic bronchitis, thus creating a further reason to avoid this nearly universal propellant. While attempts have been made to substitute other propellant gases for the fluorocarbons, these attempts have experienced problems and have not met with uniform success. Thus, there remains a need for efficient powder inhaler devices which are breath actuated.

The powder medicaments which are dispensed by powder inhaler devices of the type to which that of the present invention belongs are typically very potent and are thus delivered in relatively small doses. Consequently, it is also very important that the doses of powder medicament which are delivered be very uniform in amount, i.e., volume. Even though the total amount to be delivered may be augmented by the use of carriers and other excipients well known to the pharmaceutical formulator, it is still critical that there be a high degree of uniformity in the doses delivered.

In addition to all of the above, it is further necessary that a powder inhaler device be simple and economical to manufacture, capable of isolating the powder medicament dose in a tamper-proof and moisture-proof environment, and reliable in repeated use.

Efforts have been made in the past to create powder inhaler devices which do not rely on propellants, but which still satisfy all of the other requirements for such devices and overcome the problems outlined above. These efforts have met with varying degrees of success, as the following discussion of prior art devices makes clear.

2. Brief Description of the Prior Art

Powder inhaler devices have been used in the past which dispense unit doses of medication from prefilled capsules. However, in order for such devices to function properly, the capsule must be correctly positioned in the device which, when actuated, either punctures or pulls the capsules open. Such devices are prone to incorrect dosing, particularly by children, the elderly, and patients with impaired motor function. Moreover, pieces of the gelatin capsule shell may be dispensed with the medication.

Other devices utilize a disc with multiple cavities, each containing a unit dose of medicament covered by aluminum foil. The medication is dispensed by puncturing the aluminum foil covering the cavity. However, such devices have the disadvantage of a potential risk that small pieces of the aluminum foil might be inhaled.

SUMMARY OF THE INVENTION

In accordance with the present invention there is provided a powder inhaler device for dispensing a medicament in powder form to a patient, which is breath actuated and does not make use of a propellant, comprising (1) multiple powder medicament compartments, each compartment of sufficient size to hold a single dose of said medicament, being essentially cylindrical in shape and from 0.15 to 0.35 inch in diameter; (2) an inhalation aperture in each powder medicament compartment surrounded by a raised ridge, over which the mouth of the patient is placed when the powder medicament is dispensed by breath actuated inhalation; (3) a second inflow aperture in each said powder medicament compartment which permits ingress of air during dispensing of said powder medicament by breath actuated inhalation, said second aperture being smaller than the first, and where insufficiently small to prevent powder medicament particles from escaping, so disposed with respect to the inhalalation aperture that the powder medicament will not readily fall out of said powder medicament compartment, but always so disposed that ingress of air will aerosolize said powder medicament during breath actuated inhalation; and (4) a moisture-proof lidding material for each powder medicament compartment which sealingly covers both apertures therein, and which can be manually peeled off so as to exposed both aperatures of said powder medicament compartment for use.

The present invention further provides a powder inhaler device of the type described above in which the powder medicament compartment additionally comprises a baffle element interposed between the apertures therein which is of such size and configuration that it enhances the cyclonizing of the ingress air which aerosolizes the powder medicament.

DETAILED DESCRIPTION OF THE INVENTION

The powder inhaler device of the present invention comprises multiple powder medicament compartments. The total number of such compartments is limited by the practicality of the overall size and configuration of the device in the context of use by a patient. In its simplest form, the device may comprise a row of such compartments, from 6 to 12 or more in number. The number of compartments would be limited by the overall length which would be suitable for use by a patient. A double row would be another useful configuration for the multiple compartment arrangement, and would permit the incorporation of twice as many compartments for a given length.

In such a double row configuration, however, consideration will have to be given to the fact that the powder inhaler device of the present invention is breath actuated, and that the configuration must be such as to permit the mouth of the patient to come into a sealing relationship with the aperture in the compartment containing the powder medicament, in order for the breath actuated inhalation of the powder medicament to proceed efficiently.

Rows of compartments may be arranged into a number of different geometrical shapes to form suitable embodiments of the multiple compartment arrangement of the powder inhaler device of the present invention. For example, a triangle, square, rectangle, pentagon, hexagon, or other polygon may be formed. It is also possible to arrange the powder medicament compartments in a circular configuration.

One of the primary advantages of the powder inhaler device of the present invention is its simple design, which permits manufacture in large quantities of a rugged, reliable, and inexpensive device. The multiple powder medicament compartments may be made of any suitable material. In terms of cost, fomability, resistance to moisture and other harmful agents, weight, esthetics, and other factors, clearly the most preferred material from which to make the multiple powder madicament compartments is plastic, i.e., heat formable or moldable polymers and resins. The composition of such materials is well known in the art, and selection of a suitable material in light of the requirements mentioned above, would be well within the ordinary skill of the artisan. For example, polyethylene is an excellent material from which to make the powder inhaler device of the present invention.

The use of plastics permits the manufacture of inexpensive yet reliable powder inhaler devices conforming to the requirements of the present invention, particularly with respect to the shape and overall dimensions of the compartment which holds each individual powder medicament dose. Plastics offer many other advantages and would permit, e.g., the formation of multiple compartments in which it was possible to separate each individual compartment from every other compartment, should that be desired, by use of a thin, breakable bridging section to join the compartments together.

Each individual powder medicament compartment must be of sufficient size, i.e., volume capacity to contain a single dose of the powder medicament. Consequently, the size is dependent upon the dose of the actual drug active ingredient involved, and the additional volume of whatever carriers and excipients are used together with the actual drug active ingredient to form the overall powder medicament. While this size is variable, it will conform to the requirement that the compartment, which is essentially cylindrical in shape, be from 0.15 to 0.35 inch in diameter. Since the compartment is essentially cylindrical, increased volume is obtained by increasing the long dimension, i.e., the axial length of the cylinder. There is an upward limit on the diameter dimension of the essentially cylinder-shaped powder medicament compartment, because the compartment becomes, in fact, an aerosolization chamber in which the ingress of air during breath actuated inhalation assumes a cyclone-like shape and movement, and thereby more efficiently aerosolizes the powder medicament.

The powder medicament compartment is essentially cylindrical in shape, as has already been adverted to above in the discussion of the dimensions of the compartment. The purpose of the essentially cylindrical shape for the compartment is to permit it to function more efficiently as an aerosolization chamber, where the cylinder shape maintains or even reinforces the cyclone-like shape and movement of the air which ingresses through the inflow aperture (described further below) during breath actuated inhalation. It will be appreciated that the shape of the compartment need not be that of a perfect cylinder. It is only necessary that the shape conform to that of a cylinder to such an extent that the cyclone-like shape and movement of the ingressing air is supported, and even potentially enhanced.

The powder medicament compartment contains two apertures. The first aperture, referred to as the inhalation aperture, is the one over which the patient places his or her mouth when the powder medicament is dispensed to that patient by inhalation. The shape of the inhalation aperture is not especially critical, it may merely be essentially circular, conforming to the top of the essentially cylindrical powder medicament compartment. It need not, however, conform to the shape of that compartment, but may be an entirely different shape. It may be seqare or rectangular, for example. It is desirable, on the other hand, that its shape facilitate its function as the point at which the mouth of the patient recieves the dispensed powder medicament from the powder inhaler device. The mouth of the patient must form a sealing relationship with the inhalation aperture in order for the dispensing of the powder medicament from the device to take place efficiently, or at all. To this end, the inhalation aperture is also surrounded by a raised ridge which contributes significantly to formation of the required sealing relationship between the mouth of the patient and the inhalation aperture. The raised ridge has a second function with respect to the lidding material, which is discussed further below.

The second aperture, referred to herein as the inflow aperture, permits ingress of air during dispensing of the powder medicament by breath actuated inhalation. In comparative size, this aperture is smaller than the first, inhalation aperture. Its actual size is ultimately dependent on the size of the particles of the powder medicament. It can, however, be actually larger than the cross-sectional dimension of said particles, due to the well known bridging effect, in accordance with which particles will not flow through an opening larger than those particles. It is thus possible to calculate the maximum opening for the inflow aperture which can be utilized so as prevent the powder medicament from accidentally spilling from the powder medicament compartment when the patient uses the powder inhaler device.

Even large dimensions for the inflow aperture can be used, however. In that event, it is desirable to locate the inflow aperture in relationship to the inhalation aperture so as to prevent the powder medicament from readily falling out of the powder medicament compartment during use.

In all cases, however, the inflow aperture is always so disposed that ingress of air will aerosolize the powder medicament during breath actuated inhalation. For example, an inflow aperture located too near the inhalation aperture will fail to produce the required aerosolization of the powder medicament.

The shape of the inflow aperture is not especially critical, and a circular aperture will usually result in aerosolization of the powder medicament.

A further embodiment of the device of the present invention provides for a baffle element to be interposed between the inhalation aperture and the inflow aperture, and within the powder medicament compartment. The baffle element should be of such size and shape, and so placed, as to enhance the cyclone-like shape and movement of the ingress air which aerosolizes the powder medicament.

The final element of the powder inhaler device of the present invention is the lidding material which sealingly covers both the inhalation aperture and the inflow aperture of the powder medicament compartment. The material must be moisture-proof, and its sealing of the apertures of the powder medicament compartment must also provide a moisture-proof seal. This requirement is straightforward, since clearly moisture, if permited access to the powder medicament, would soon render it incapable of being aerosolized.

The lidding material must also be capable of being manually peeled off so as to expose both apertures of the powder medicament compartment, making the powder inhaler device ready for use by the patient. A material which readily satisfies these requirements for the lidding material and is very inexpensive to use, is an aluminum foil with a heat-sealable film backing that can be peeled off. Heat-sealable film materials are well known and particles of the powder medicament will not adhere to them, which is necessary since those particles will be exposed to that heat-sealable film meterial when the lidding material sealingly covers both apertures of the powder medicament compartment. Such heat-sealable film backed aluminum foils and other material fulfilling the same requirements are well known in the packaging art, as are the techniques by which they are applied, and would be readily apparent to the skilled artisan.

DESCRIPTION OF THE DRAWINGS

The drawings (FIGS. 1 and 2) depict particular embodiments of the powder inhalation device of the present invention, but nothing in those drawings is intended to be a limitation of the scope of the present invention.

In FIG. 1 multiple powder medicament compartments configured in a row 1, consist of individual powder medicament compartments. A typical compartment is 3, which contains an inhalation aperture 5, and an inflow aperture 7. The inhalation aperture 5 leads to the cavity comprising the compartment(not fully shown) which holds the individual dose of powder medicament. The inflow 7 permits ingress of air which aerosolizes the powder medicament. Before the powder inhaler device is to be used, the apertures in each powder medicament compartment must be sealed by a lidding material 9. This must consist of a mositure-proof material such as aluminum foil which has a heat-sealable film backing 11 that will provide a moisture-proof seal while the lidding material sealingly covers both apertures, but which permits the lidding material to be peeled off, exposing the apertures in the powder medicament compartment.

In FIG. 2 the mouth 14 of a patient 16 has been placed over the inhalation aperture 5 of the powder medicament compartment 3. The powder inhaler device is breath actuated, so that when the patient 16 inhales, a vacuum or reduced pressure zone is created at the inhalation aperture 5, causing air (depicted by the arrows) to enter the inflow aperture 7 and pass over and around the baffle element 18. Within the cavity of the powder medicament compartment 3, the cyclone-like shape and movement of the air aerosolizes the powder modicament 20. This aerosol of powder medicament then passes down the trachea of patient 16 to reach the point of administration, the bronchi and other parts of the lung (not shown).

Figure 1:
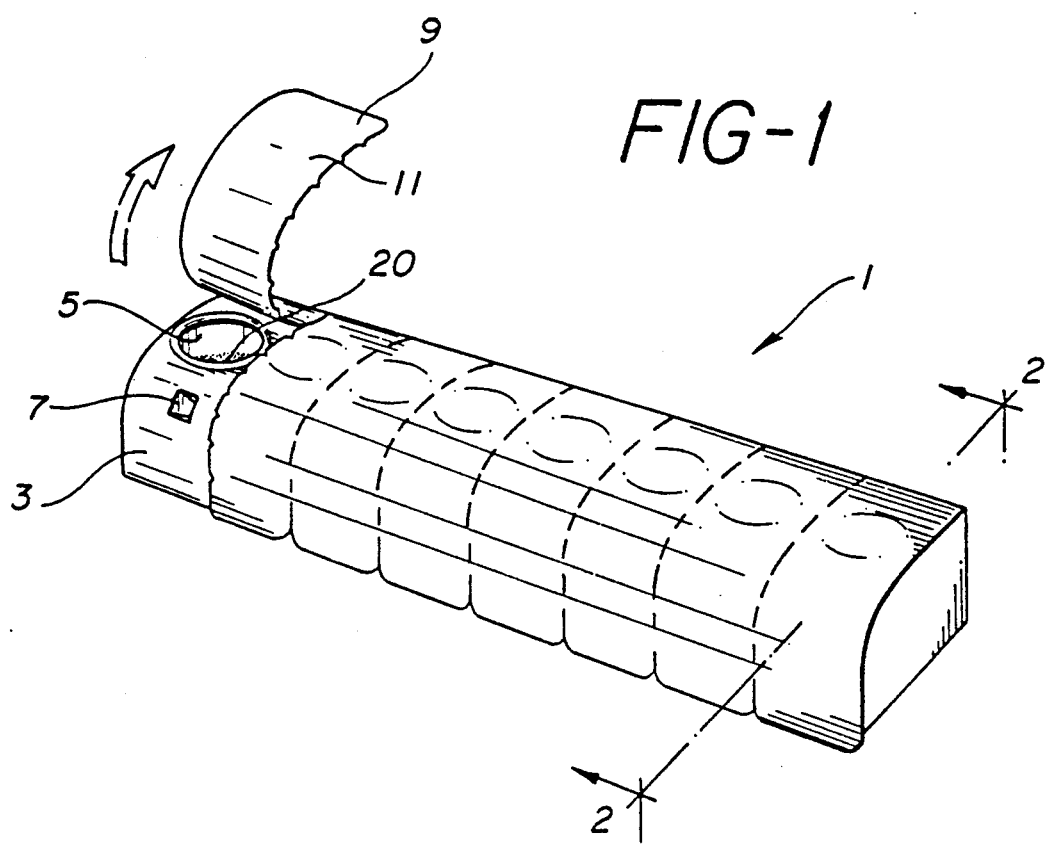
FIG. 1 depicts a row configuration of multiple powder medicament compartments.
Figure 2:
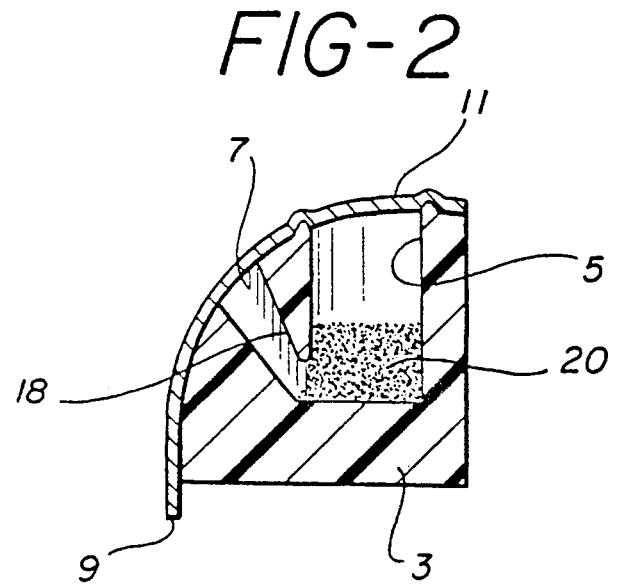
FIG. 2 depicts use by a patient of one such individual powder medicament compartment.
Figure 3:
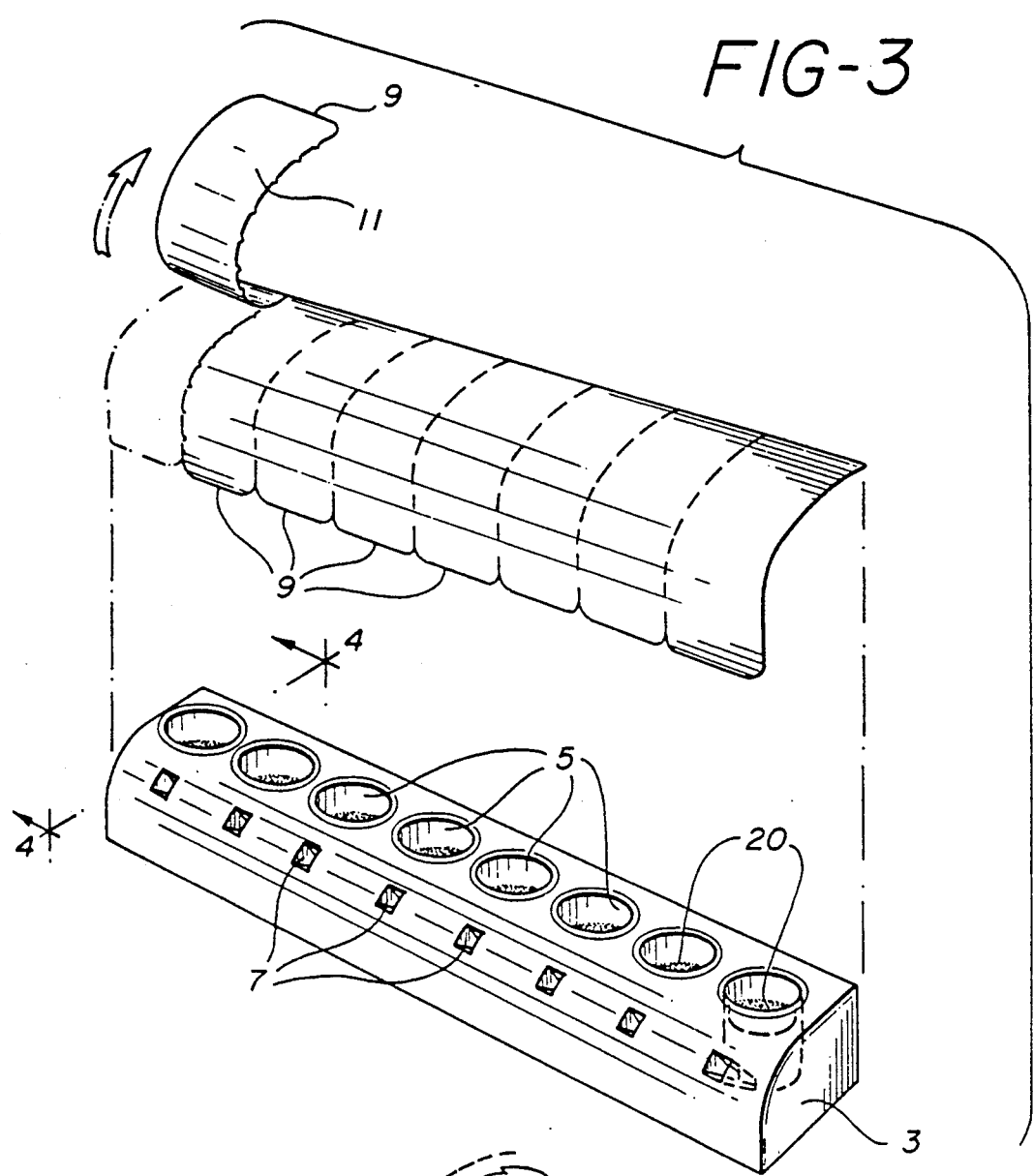
Figure 4:
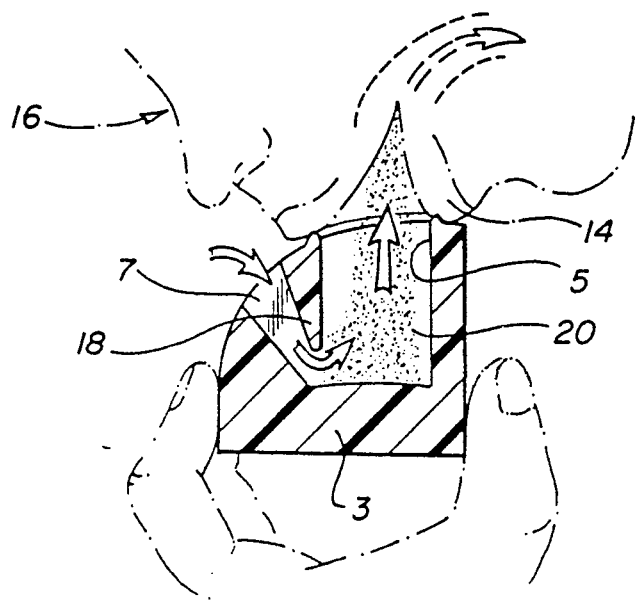

What is claimed is:

1. A powder inhaler device for dispensing a medicament in powder form to a patient, which is breath actuated and does not make use of a propellant, comprising (1) multiple powder medicament compartments, each compartment of sufficicent size to hold a single dose of said medicament, being essentially cylindrical in shape and from 0.15 to 0.35 inch in diameter; (2) first inhalation aperture in each powder medicament compartment surrounded by a reised ridge, over which the mouth of the patient is placed when the powder medicament is dispensed by breath actuated inhalation; (3) a second inflow aperture in each said powder medicament compartment said powder disposed with respect to the inhalalation aperture so that the powder medicament will not readily fall out of said powder medicament compartment, but always so disposed that ingress of air will aerosolize said powder medicament during breath actuated inhalation; and (4) a moisture-proof lidding material for each powder medicament compartment which sealingly covers both apertures therein, and which can be manually peeled off so as to expose both aperture of said powder medicament compartment for use.

2. A powder inhaler device according to claim 1 in whicht the powder medicament compartment additionally comprises a baffle element interposed between the apertures therein which is of such size and configuration that it enhances the cyclonizing of the ingress air which aerosolizes the powder medicament.

3. A powder inhaler device according to claim 1 in which the lidding material consists of aluminum foil with a heat-sealable film backing such that it will provide a moisture-proof seal while the lidding material sealingly covers both apertures of the powder medicament compartment, while permitting the lidding material to be peeled off, exposing said apertures, but such that the powder medicament will not adhere thereto.

4. A powder inhaler device according to claim 1 wherein the configuration of the multiple powder medicament compartments is a row.

* * * * *